(12) United States Patent
Tian

(10) Patent No.: US 9,382,478 B2
(45) Date of Patent: *Jul. 5, 2016

(54) LIQUID CRYSTAL COMPOSITION AND METHODS FOR THE PREPARATION THEREOF

(71) Applicant: BOE Technology Group Co., Ltd., Beijing (CN)

(72) Inventor: Xiaoxiong Tian, Beijing (CN)

(73) Assignee: Boe Technology Group Co., Ltd., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/500,519

(22) Filed: Sep. 29, 2014

(65) Prior Publication Data

US 2015/0344779 A1  Dec. 3, 2015

(30) Foreign Application Priority Data

May 29, 2014  (CN) .......................... 2014 1 0234526

(51) Int. Cl.

| C07C 13/66 | (2006.01) |
|---|---|
| C09K 19/32 | (2006.01) |
| C07C 17/02 | (2006.01) |
| C07D 263/52 | (2006.01) |
| C07C 45/59 | (2006.01) |
| C07C 45/61 | (2006.01) |
| C07C 1/20 | (2006.01) |

(52) U.S. Cl.
CPC . *C09K 19/32* (2013.01); *C07C 1/20* (2013.01); *C07C 13/66* (2013.01); *C07C 17/02* (2013.01); *C07C 45/59* (2013.01); *C07C 45/61* (2013.01); *C07D 263/52* (2013.01); *C07C 2103/42* (2013.01)

(58) Field of Classification Search
CPC .................................................... C07D 331/04
See application file for complete search history.

(56) References Cited

U.S. PATENT DOCUMENTS

2008/0100208 A1   5/2008   Shin et al.

FOREIGN PATENT DOCUMENTS

| CN | 101489961 | 7/2009 |
|---|---|---|
| CN | 103146375 | 6/2013 |
| CN | 103805166 | 5/2014 |
| CN | 104017585 | 9/2014 |
| WO | 2012/141197 | 10/2012 |

*Primary Examiner* — Chanceity Robinson
(74) *Attorney, Agent, or Firm* — Calfee, Halter & Griswold LLP

(57) ABSTRACT

The disclosure relates to a liquid crystal compound having a structure of the general formula P2, wherein, $R_1$ represents C1-C6 alkyl, $R_2$ and $R_3$, which are identical or different, independently represent C1-C6 alkyl, and $R_4$ represents C2-C6 alkenyl. The disclosure also relates to a preparation process of the liquid crystal compound, a liquid crystal composition comprising the liquid crystal compound, and a liquid crystal display panel comprising the liquid crystal compound.

7 Claims, 1 Drawing Sheet

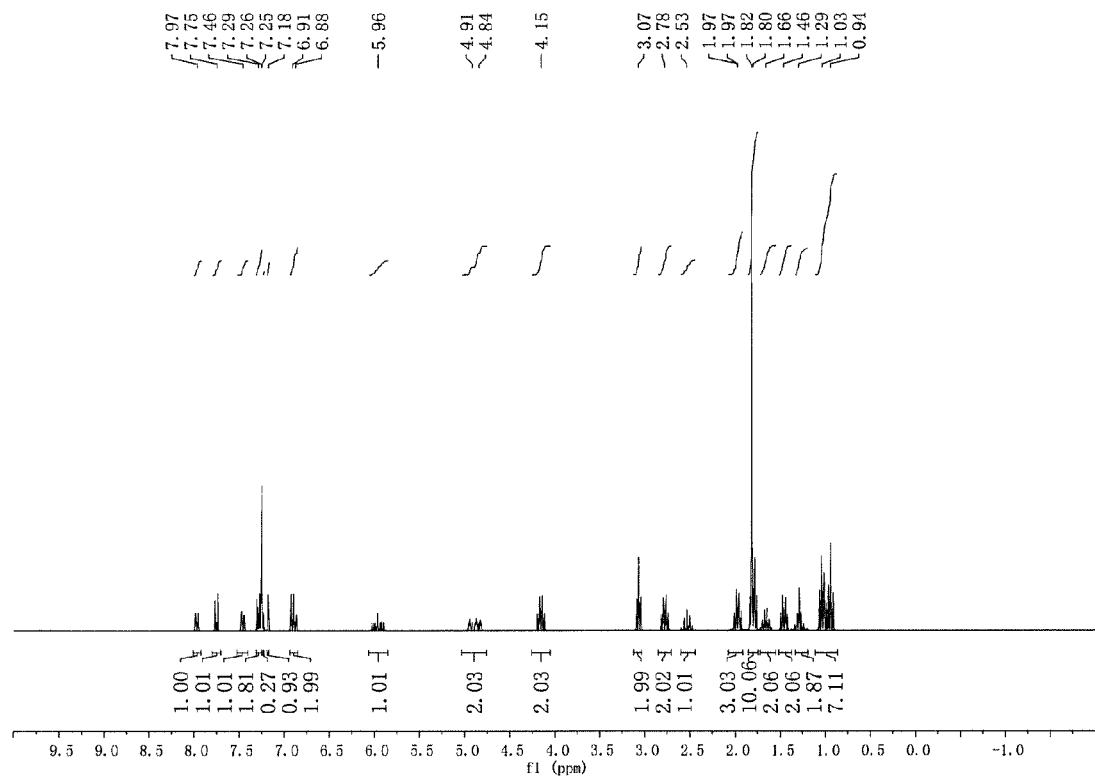

LIQUID CRYSTAL COMPOSITION AND METHODS FOR THE PREPARATION THEREOF

RELATED APPLICATIONS

The present application claims the benefit of Chinese Patent Application No. 201410234526.6, filed May 29, 2014, the entire disclosure of which is incorporated herein by reference.

FIELD

The general inventive concepts relate to the field of liquid crystal display, and more particularly to a liquid crystal compound and processes for preparation thereof.

BACKGROUND

In the realm of flat panel display devices, a thin film transistor liquid crystal display (Thin Film Transistor Liquid Crystal Display, TFT-LCD for short) generally has the characteristics of small volume, low power consumption, low manufacture cost, no radiation, and so on, and occupies a dominant position in the current market of flat panel display.

Liquid crystal displays are been widely used in modern life. With the development of liquid crystal display technology, a variety of liquid crystal compounds have been practically applied. The properties of the respective liquid crystal compound itself, including phase change temperature, optical anisotropy, dielectric anisotropy, viscosity and electric resistance, can have a great influence on the final application of the liquid crystal material. The development of new liquid crystal compounds and new compositions containing the liquid crystal compounds are very important for continuing to improve the various properties of liquid crystal materials, and correspondingly improving the quality of liquid crystal displays.

Generally speaking, the clearing point of existing liquid crystal materials is relatively low, about 100° C., which seriously affects the application scope of the liquid crystal display. So there is still a need for liquid crystal materials with a high clearing point.

SUMMARY

The present disclosure provides liquid crystal compounds, compositions, methods for making the compounds, as well as display devices incorporating the compounds or compositions. The compounds, compositions, and display devices may avoid, or otherwise alleviate, one or more of the drawbacks of conventional display devices.

To this end, an object of the general inventive concepts is to provide a liquid crystal compound and methods for preparation thereof, a liquid crystal composition containing the liquid crystal compound and a preparation process thereof, and a liquid crystal display panel containing the liquid crystal compound. Since the liquid crystal compound has a high clearing point, the application scope of the liquid crystal materials containing the liquid crystal compound can be broadened greatly.

The disclosure firstly relates to a new liquid crystal compound of 7-hydrogen benzo[de]anthracene type, of which the structure corresponds to the following general formula P2 (hereinafter also called "liquid crystal compound P2" or "compound P2"):

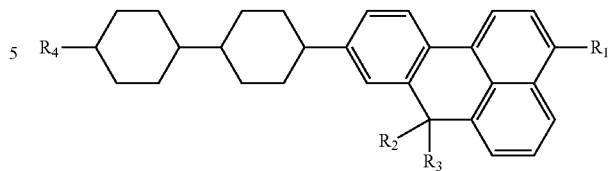

wherein, R1 represents C1-C6 alkyl, R2 and R3, which are identical or different, independently represent C1-C6 alkyl, R4 represents C2-C6 alkenyl.

The disclosure also relates to a preparation process of the liquid crystal compound P2, which comprises the following steps: (a) conducting a bromination of compound P2-1 by N-bromosuccinimide (NBS) in tetrahydrofuran to obtain compound P2-2 as follows:

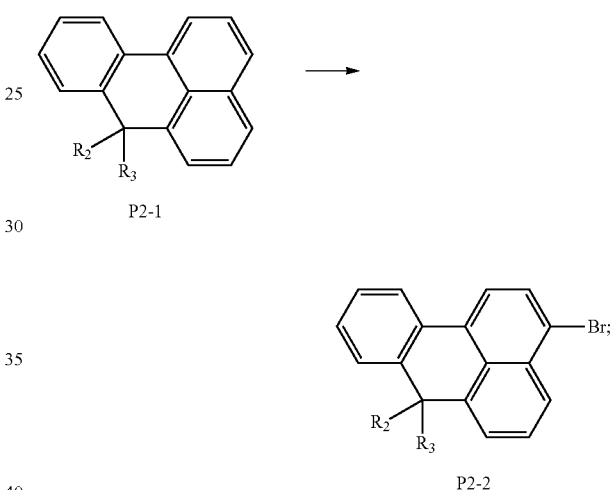

(b) reacting compound P2-2 obtained in step (a) with C1-C6 alkyl magnesium bromide in toluene in the presence of a catalyst, to obtain compound P2-3 as follows:

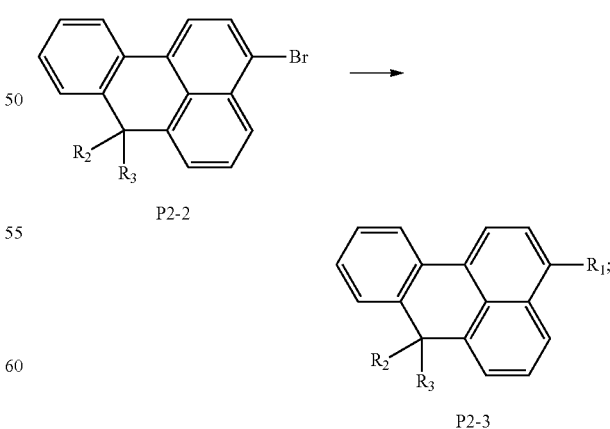

(c) brominating compound P2-3 obtained in step (b) with bromine in tetrahydrofuran, to obtain compound P2-4 shown as follows:

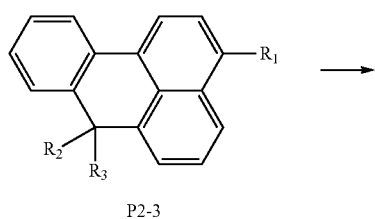

P2-3

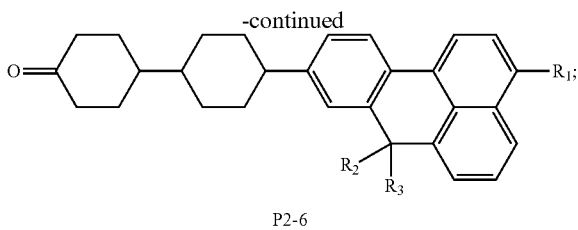

P2-6

(f) conducting a Wittig reaction with compound P2-6 and (methoxymethyl)triphenyl phosphonium chloride and potassium t-butoxide, followed by a hydrolysis reaction with hydrochloric acid, to obtain compound P2-7 as follows:

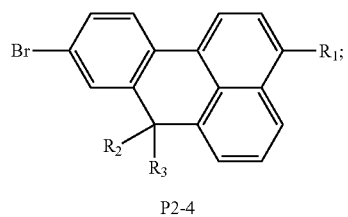

P2-4

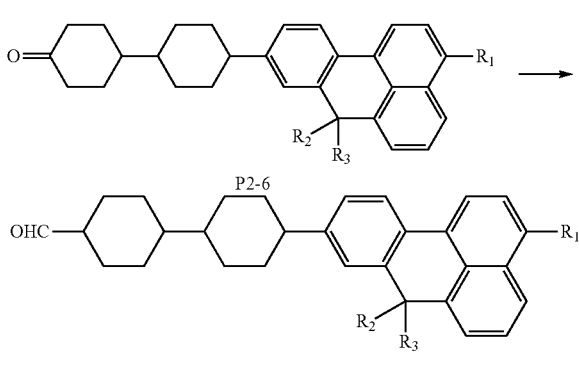

P2-7

(d) preparing a Grignard reagent from compound P2-4, then conducting an addition reaction of the Grignard reagent to compound

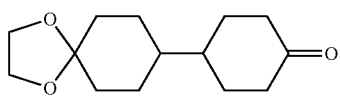

in tetrahydrofuran, a dehydration, then a reduction reaction, to obtain compound P2-5 as follows:

(g) conducting a Wittig reaction of compound P2-7 with C1-C5 alkyl triphenyl phosphonium bromide and potassium t-butoxide, to obtain compound P2 as follows:

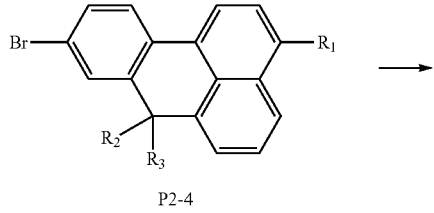

P2-4

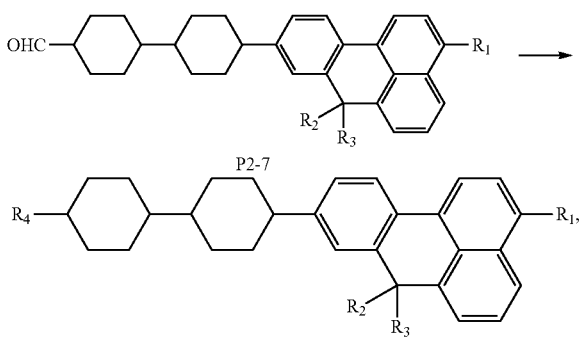

P2

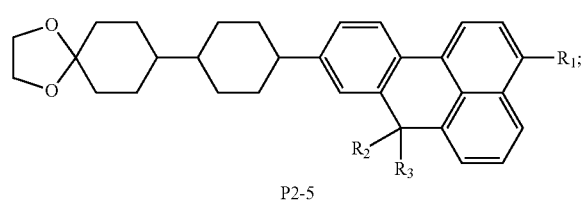

P2-5 wherein, R1, R2, R3 and R4 are as above defined.

The general inventive concepts also relate to a liquid crystal composition comprising at least one of the liquid crystal compounds as above defined.

The general inventive concepts also relate to methods for the preparation of the liquid crystal composition, including a step for mixing all the components of the liquid crystal composition according to the weight percentages discussed herein.

(e) hydrolyzing compound P2-5 in toluene with formic acid, to obtain compound P2-6 as follows:

The disclosure finally relates to a liquid crystal display panel, which comprises at least one liquid crystal compound P2 as defined above.

BRIEF DESCRIPTION OF THE DRAWING

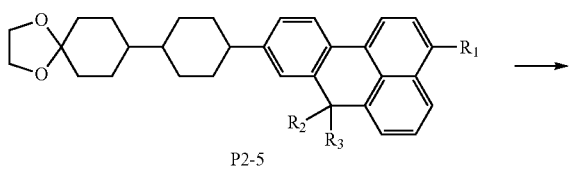

P2-5

Several technical aspects of the present disclosure will be described in more detail below with reference to the accom- FIG. 1 represents the 1H-NMR spectrum of the liquid crystal compound obtained in Example 1.

DETAILED DESCRIPTION

The present invention and associated general inventive concepts will be further described hereinafter in detail with reference to the accompanying drawings and various exemplary embodiments. One of ordinary skill in the art will appreciate that these exemplary embodiments only constitute a fraction of the possible embodiments encompassed by the present invention and associated general inventive concepts. As such, the scope of the present disclosure is by no means limited to the exemplary embodiments set forth herein.

In order to widen the potential scope of use of liquid crystal materials, this disclosure provides a new liquid crystal compound having a relative high clearing point. It was discovered that, liquid crystal compound P2, when it contains a bi-cyclohexyl, has a clearing point much higher than the liquid crystal compound containing cyclohexyl instead of bi-cyclohexyl. This finding is unexpected to those skilled in the art, because those skilled in the art generally believe the clearing point of liquid crystal compound generally is affected strongly by the core structure of the compound (for example for liquid crystal compound P2, the core structure represents 7-hydrogen benzo[de]anthracene), and generally the substituent group (here the bi-cyclohexyl group) has little effect on the clearing point of the liquid crystal compound. Furthermore, it has been found surprisingly found that liquid crystal compound P2, in which the substituent group R4 is unsaturated groups, such as alkenyl, has a relatively higher clearing point than the compound, in which R4 is a saturated group, such as alkyl. This founding is also unexpected to those skilled in the art. The liquid crystal material made of the liquid crystal compound P2 has a clearing point higher than 130° C., much higher than that of the existing liquid crystal materials. The higher clearing point can greatly broaden the application scope of liquid crystal display panels incorporating the compounds.

In certain exemplary embodiments, a liquid crystal compound is provided having the following structural formula, P2:

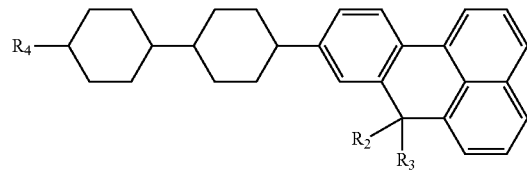

P2 wherein, R1 represents C1-C6 alkyl, R2 and R3, which are identical or different, independently represent C1-C6 alkyl, and R4 represents C2-C6 alkenyl.

According to certain exemplary embodiments, R1 represents C2-C4 alkyl, R2 and R3, which are identical or different, independently represent C1-C3 alkyl, R4 represents C2-C3 alkenyl.

In certain exemplary embodiments, the liquid crystal compound has a structure of the following general formula:

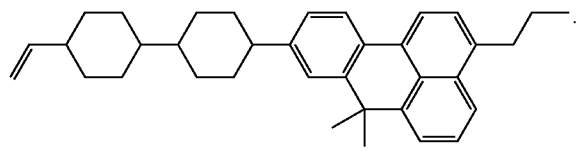

Compound P2 is a new liquid crystal compound of 7-hydrogenbenzo[de]anthracene type, which has a higher clearing point, good physical and chemical stability, and the liquid crystal compound can greatly broaden the application scope of liquid crystal display panels.

Also provided are methods for the preparation of liquid crystal compounds, which method comprises the following steps:

(a) brominating compound P2-1 by N-bromosuccinimide (NBS) in tetrahydrofuran to obtain compound P2-2; wherein the molar ratio of compound P2-1 to NBS is 1:1 to 1:1.1, the reaction temperature is 17 to 60° C., and the reaction time is 20 to 80 minutes, as follows:

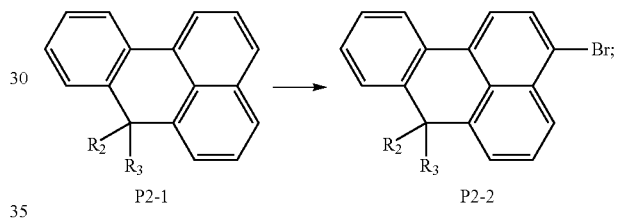

(b) reacting compound P2-2 obtained in step (a) with C1-C6 alkyl magnesium bromide in toluene in the presence of a catalyst tetrakis(triphenylphosphine)palladium(0), to obtain compound P2-3; wherein the molar ratio of compound P2-2 to the C1-C6 alkyl magnesium bromide is 1:1.5 to 1:5, the reaction temperature is 0 to 40° C., and the reaction time is 1 to 8 hours, as follows:

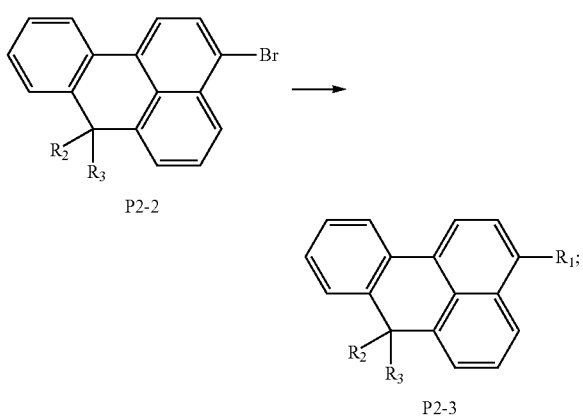

(c) brominating compound P2-3 obtained in step (b) with bromine in tetrahydrofuran to obtain compound P2-4; wherein the molar ratio of compound P2-3 to bromine is 1:1 to 1:1.5, the reaction temperature is 0 to 20° C., and the reaction time is 1 to 8 hours, as follows:

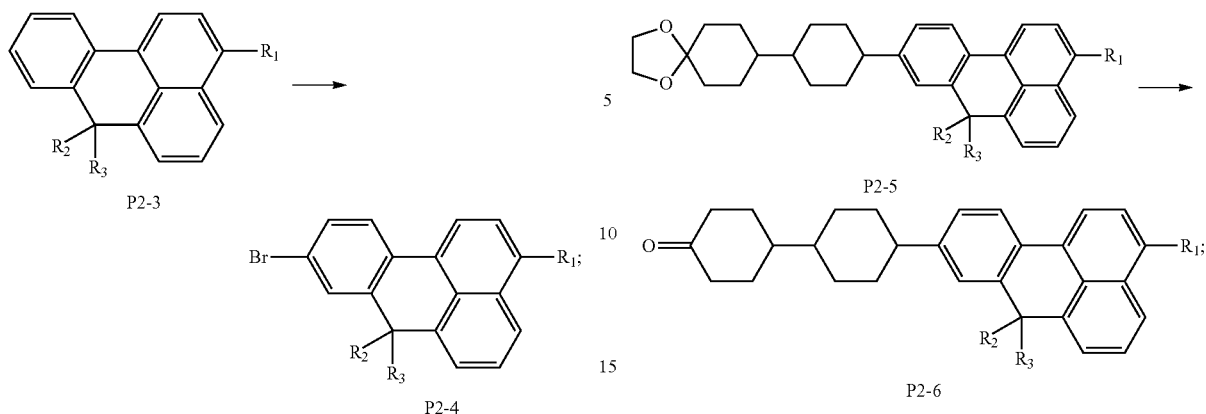

(d) preparing a Grignard reagent from compound P2-4, then conducting an addition reaction of the Grignard reagent with compound

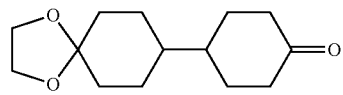

in tetrahydrofuran, followed by a dehydration reaction, and then a reduction reaction, to obtain compound P2-5; wherein the molar ratio of compound P2-4 to compound

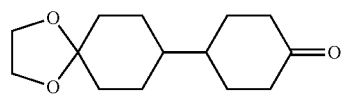

is 1:1 to 1:1.2, the reaction temperature is 10 to 80° C., and the reaction time is 1 to 5 hours, as follows:

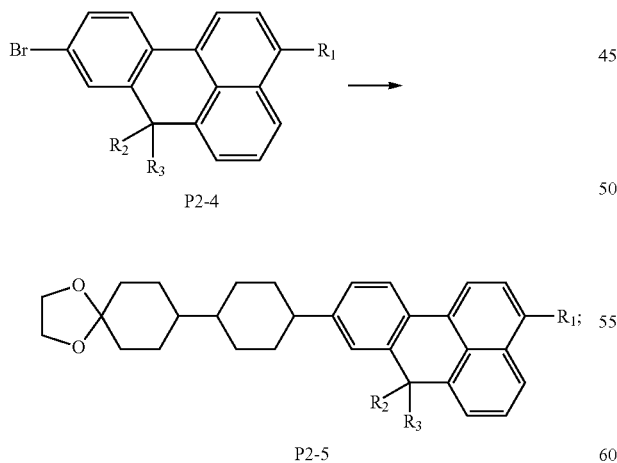

(e) hydrolyzing compound P2-5 obtained in step (d) in toluene with formic acid, to obtain compound P2-6; wherein the molar ratio of compound P2-5 to formic acid is 1:1 to 1:1.2, the reaction temperature is 25 to 80° C., and the reaction time is 30 to 60 minutes, as follows:

(f) conducting a Wittig reaction of compound P2-6 obtained in step (e), with (methoxymethyl)triphenyl phosphonium chloride and potassium t-butoxide, and then a hydrolysis reaction with hydrochloric acid, to obtain compound P2-7; wherein the molar ratio of compound P2-6 to the (methoxymethyl)triphenyl phosphonium chloride is 1:1 to 1:1.2, the molar ratio of compound P2-6 to potassium t-butoxide is 1:1 to 1:1.5, the reaction temperature is 0 to 25° C., and the reaction time is 1 to 6 hours, as follows:

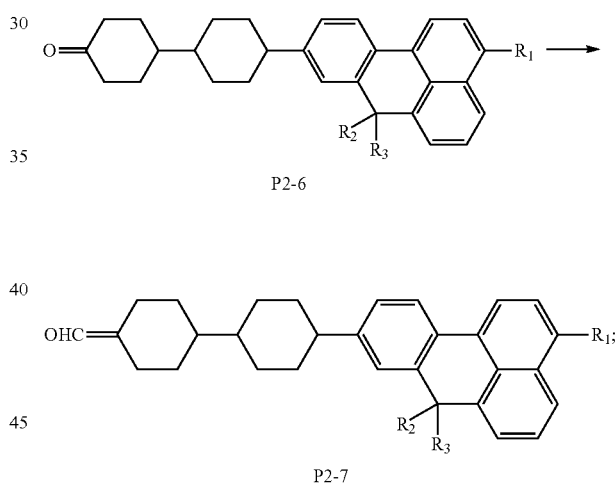

(g) conducting a Wittig reaction of compound P2-7 with C1-C5 alkyl triphenyl phosphonium bromide and potassium t-butoxide, to obtain compound P2; wherein the molar ratio of compound P2-7 to C1-C5 alkyl triphenyl phosphonium bromide is 1:1 to 1:1.2, the molar ratio of compound P2-7 to potassium t-butoxide is 1:1 to 1:1.5, the reaction temperature is 0 to 25° C., and the reaction time is 1 to 5 hours, as follows:

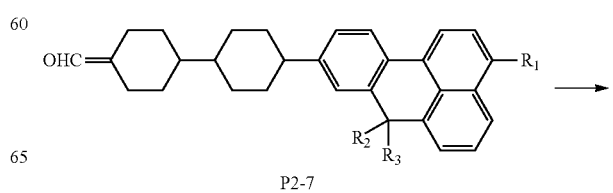

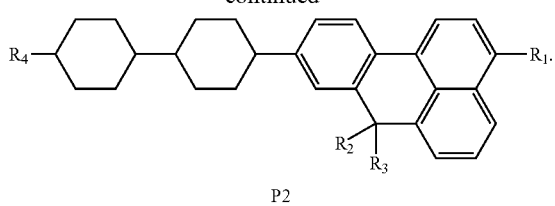

P2

In certain exemplary embodiments: (a) the molar ratio of compound P2-1 to N-bromosuccinimide is 1:1 to 1:1.05, the reaction temperature is 40° C., and the reaction time is 30 to 40 minutes;

(b) the molar ratio of compound P2-2 to the C1-C6 alkyl magnesium bromide is 1:1.5 to 1:2, the reaction temperature is 30° C., and the reaction time is 3 hours;

(c) the molar ratio of compound P2-3 to bromine is 1:1 to 1:1.2, the reaction temperature is 10° C., and the reaction time is 2 to 5 hours;

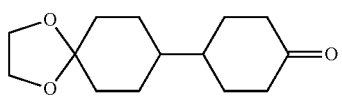

(d) the molar ratio of compound P2-4 to compound is 1:1 to 1:1.1, the reaction temperature is 60° C., and the reaction time is 3 hours;

(e) the molar ratio of compound P2-5 to formic acid is 1:1 to 1:1.1, the reaction temperature is 65° C., and the reaction time is 40 to 50 minutes;

(f) the molar ratio of compound P2-6 to (methoxymethyl) triphenyl phosphonium chloride is 1:1 to 1:1.1, the molar ratio of compound P2-6 to potassium t-butoxide is 1:1 to 1:1.2, the reaction temperature is 10° C., and the reaction time is 5 hours;

(g) the molar ratio of compound P2-7 to the C1-C5 alkyl triphenyl phosphonium bromide is 1:1 to 1:1.1, the molar ratio of compound P2-7 to potassium t-butoxide is 1:1 to 1:1.2, the reaction temperature is 10° C., and the reaction time is 3 hours.

In certain exemplary embodiments, the C1-C5 alkyl triphenyl phosphonium bromide is methyltriphenyl phosphonium bromide.

The general inventive concepts also relate to a liquid crystal composition comprising at least one of liquid crystal compound as above defined.

In an exemplary embodiment, the liquid crystal composition comprises 5% to 40% by weight of at least one liquid crystal compound P2, relative to the total weight of the liquid crystal composition.

In an exemplary embodiment, the liquid crystal composition comprises 20% to 40% by weight of at least one liquid crystal compound P2, relative to the total weight of the liquid crystal composition.

In an exemplary embodiment, the liquid crystal composition, in addition to 20% to 40% by weight, preferably 24% to 33% by weight of liquid crystal compound P2, also comprises:

2% to 8% by weight, preferably 4% to 7% by weight of compound A:

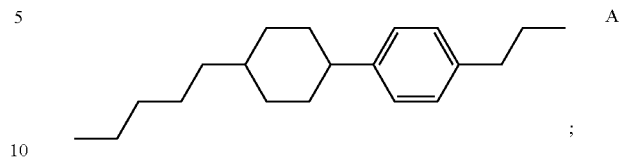

8% to 19% by weight, preferably 10% to 16% by weight of compound B:

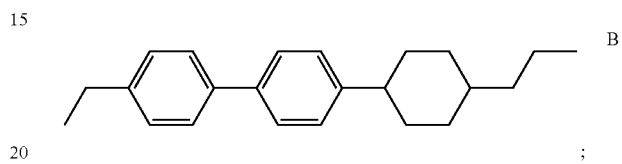

10% to 20% by weight, preferably 13% to 17% by weight of compound C:

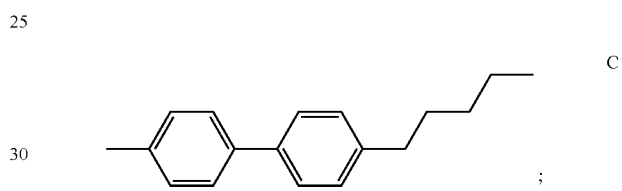

15% to 30% by weight, preferably 17% to 25% by weight of compound D:

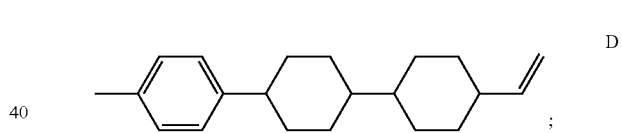

8% to 20% by weight, preferably 8% to 18% by weight of compound E:

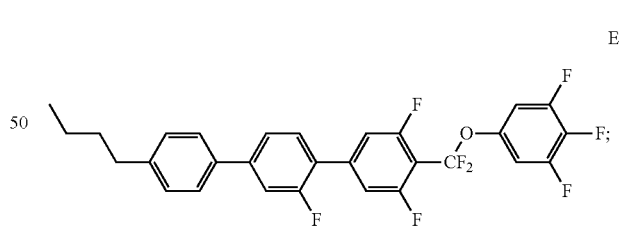

5% to 15% by weight, preferably 7% to 12% by weight of compound F:

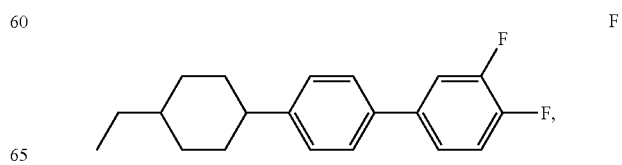

relative to the total weight of the liquid crystal composition.

In an exemplary embodiment, the liquid crystal composition comprises 6% by weight of compound A, 15% by weight of compound B, 15% by weight of compound C, 20% by weight of compound D, 10% by weight of compound E, 9% by weight of compound F, and 25% by weight of liquid crystal compound P2, relative to the total weight of the liquid crystal composition.

The general inventive concepts also relate to a liquid crystal composition, wherein the liquid crystal composition comprises 5% to 20% by weight of liquid crystal compound P2, relative to the total weight of the liquid crystal composition.

In an exemplary embodiment, the liquid crystal composition, in addition to 5% to 20% by weight, preferably 6% to 14% by weight of liquid crystal compound P2, also comprises:

3% to 10% by weight, preferably 4% to 8% by weight of compound A

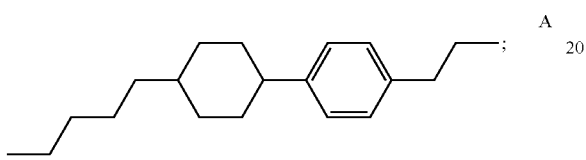

8% to 15% by weight, preferably 10% to 13% by weight of compound B:

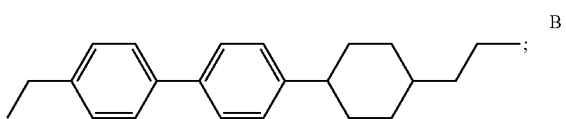 [SMILES: CCCC1CCC(c2ccc(-c3ccc(CC)cc3)cc2)CC1]

7% to 18% by weight, preferably 10% to 15% by weight of compound C:

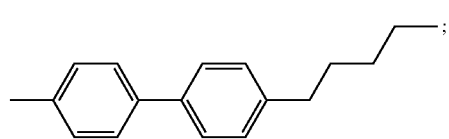

5% to 30% by weight, preferably 10% to 20% by weight of compound D

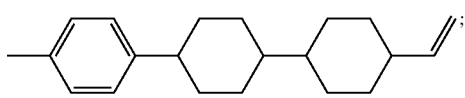

5% to 20% by weight, preferably 7% to 13% by weight of compound E:

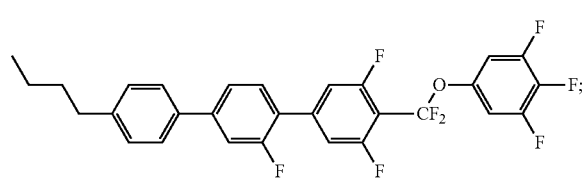

5% to 15% by weight, preferably 6% to 12% by weight of compound F:

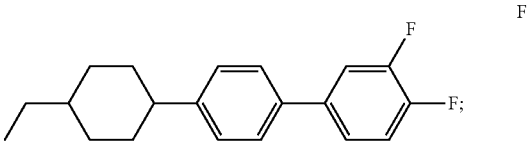 [SMILES: CCC1CCC(c2ccc(-c3ccc(F)c(F)c3)cc2)CC1]

5% to 30% by weight, preferably 7% to 20% by weight of compound G:

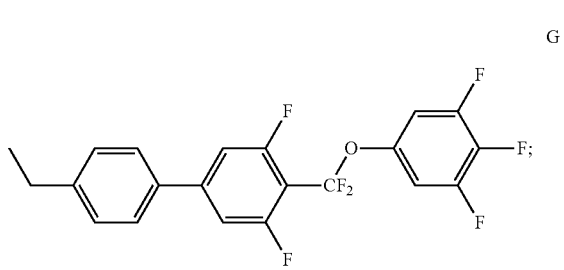 [SMILES: CCc1ccc(-c2cc(F)c(C(F)(F)Oc3cc(F)c(F)c(F)c3)c(F)c2)cc1]

15% to 30% by weight, preferably 20% to 26% by weight of compound P1:

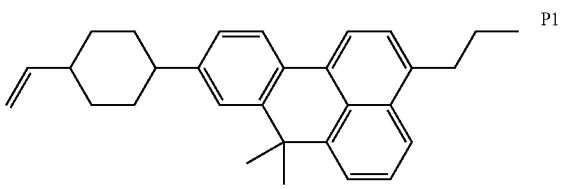 [SMILES: C=CC1CCC(c2ccc3c(c2)C(C)(C)c2cccc4c(CCC)ccc-3c24)CC1]

relative to the total weight of the liquid crystal composition.

In an exemplary embodiment, the liquid crystal composition comprises 5% by weight of compound A, 12% by weight of compound B, 12% by weight of compound C, 12% by weight of compound D, 10% by weight of compound E, 8% by weight of compound F, 9% by weight of compound G, 23% by weight of compound of P1, and 9% by weight of liquid crystal compound P2, relative to the total weight of the liquid crystal composition.

The general inventive concepts also relate to methods for the preparation liquid crystal compositions, including a step for mixing the compounds of the liquid crystal composition. More specifically, the liquid crystal composition is obtained by mixing all components of the composition according to the contents as defined above in any order.

The general inventive concepts also relate to a liquid crystal display panel, wherein the liquid crystal display panel comprises at least one of: a liquid crystal compound P2 as defined above, and a liquid crystal composition as defined above.

In an exemplary embodiment, the liquid crystal display panel comprises a first substrate, a second substrate placed on a box, and a liquid crystal layer located between the first substrate and the second substrate, wherein the liquid crystal layer comprises at least one of: a liquid crystal compound P2 as defined above, and a liquid crystal composition as defined above.

In order to understand the advantages of the exemplary embodiments more clearly, non-limiting examples are given below.

EXAMPLES

Synthesis Example 1

Preparation of the Compound of the Following Formula 2-8

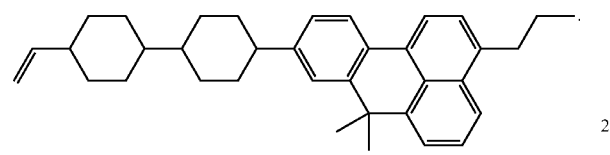

2-8

The synthesis process is as follows:

(a) in a round bottom flask, 2.5 g of compound 2-1 is dissolved in 50 ml of tetrahydrofuran, then 2.0 g of N-bromosuccinimide (NBS) was added under stirring to carry out a bromination reaction at temperature of 40° C. After the reaction ended, 80 ml of water was added, and yellowish solid precipitate was produced. The solid was filtered, dried and analyzed by NMR and mass spectrometry. The analysis showed that the obtained solid has structural formula 2-2; wherein the reaction is as follows:

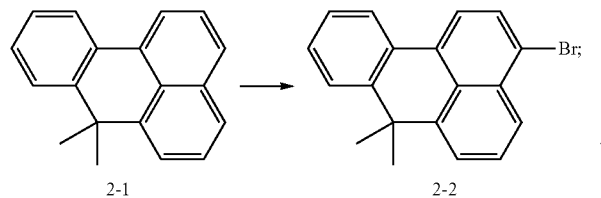

2-1    2-2

(b) at room temperature, 2.9 g of 2-2 obtained in step (a) and 50 ml of toluene were added into a round bottom flask, then a catalytic amount (0.1 g) of catalyst tetrakis(triphenylphosphine)palladium was added with stirring. The temperature was controlled at 30° C. 27 g of 15% solution of propyl magnesium bromide in ether was added dropwise to conduct a reaction. After 3 hours, a proper amount of water was added and the organic phase was separated in separating funnel. Then the organic phase was decolorized by using silica gel column, then subjected to an evaporation to remove the solvent followed by vacuum distillation. The obtained product was determined by NMR and mass spectrometry to have formula 2-3; wherein the reaction is shown as follows:

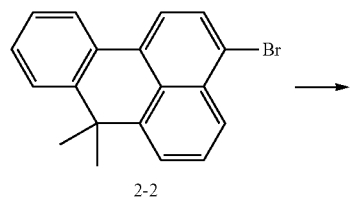

2-2

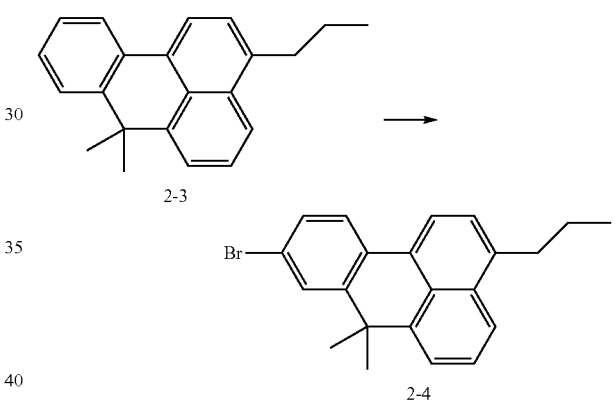

2-3

(c) in a round bottom flask, 2.55 g of 2-3 obtained in step (b) was dissolved in 50 ml of tetrahydrofuran under stirring, and the temperature was controlled at 10° C. Then 1.2 g of bromine was added under stirring to conduct a bromination reaction, wherein the reaction time was 2 hours. After the reaction was finished, the obtained reaction mixture was washed with 10% sodium sulfite solution. After a phase separation, the organic phase was decolorized by silica gel column and subjected to an evaporation to remove the solvent. The obtained product was subjected to a recrystallization in 50/50 ethanol/toluene. The obtained crystal was determined by NMR and mass spectrometry to have formula 2-4; wherein the reaction is shown as follows:

2-3

2-4

(d) 0.28 g of metal magnesium powder, 5 ml tetrahydrofuran, a small amount of 1,2-dibromoethane were added into a three-necked bottle. To this was added a mixture of 3.5 g of 2-4 and 30 ml tetrahydrofuran was added dropwise. After the addition, the reaction medium was heated to reflux for 30 minutes, to obtain a Grignard reagent solution. Then the Grignard reagent solution was cooled to 20° C., and a mixture of 2.7 g

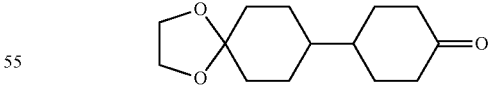

and 10 ml tetrahydrofuran was added dropwise. After the addition, the reaction medium was heated to reflux for 30 min, then cooled to room temperature. A solution of ammonium chloride was added to conduct a hydrolysis reaction. After the hydrolysis reaction was complete, the organic phase was separated in separating funnel and then concentrated to dryness. Then 100 ml of toluene, 1 g p-toluene sulfonic acid, 0.5 grams of ethylene glycol were added, then the mixture was heated to reflux for 5 hours to conduct a dehydration, wherein the water produced by the dehydration was removed by azeotropy. After the dehydration was finished, the mixture was cooled to the room temperature and an appropriate amount of water was added hereinto for conducting a wash and the organic phase was separated in separating funnel. Then the organic phase was concentrated to dryness, and subjected to a crystallization in ethanol to obtain an intermediate containing an ethylenic bond.

The intermediate was dissolved in the 50/50 mixture of toluene/ethyl acetate, and a catalytic amount of Pd/C was added; nitrogen was injected into the reactor to replace the air in the reactor, then hydrogen was injected to replace the nitrogen present in the reactor. The pressure of hydrogen was maintained at 0.1 MPa in the reactor for 1 hour. After the reduction by hydrogen, the catalyst was removed by filtration, and the organic phase was concentrated to dryness and subjected to a recrystallization in the 60/40 mixture of ethanol/toluene, to obtain the intermediate of formula 2-5:

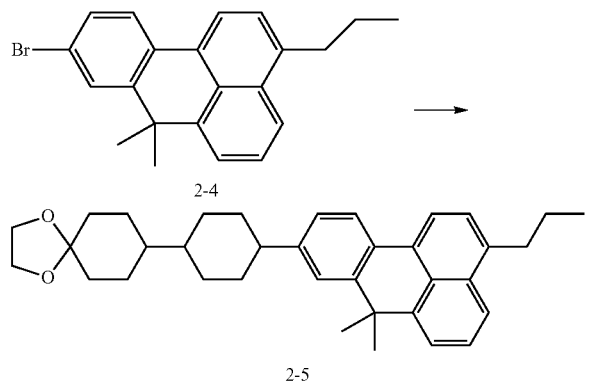

(e) in a round bottom flask, 4.5 g of intermediate 2-5 obtained in Step (d) were dissolved in 50 ml toluene under stirring, and the mixture was heated to 65° C. Then 80% formic acid aqueous solution (containing 0.01 mol formic acid) was added to carry out a hydrolysis reaction. The hydrolysis reaction time was 50 minutes, and the reaction temperature was maintained at 65° C. Then the reaction mixture was subjected to a phase separation and the organic phase was washed with water and was concentrated to dryness, to obtain the intermediate of formula 2-6; wherein the reaction is shown as follows:

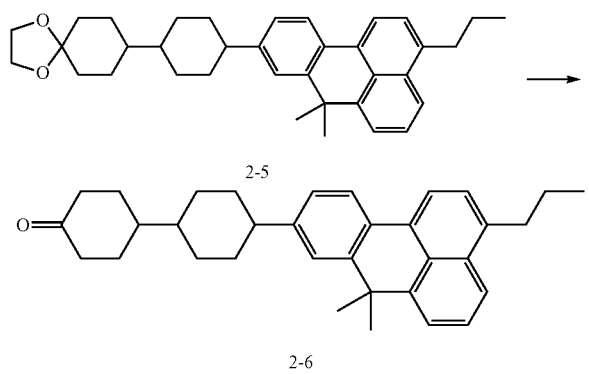

(f) 50 ml tetrahydrofuran and 2.8 g methoxymethyl triphenyl phosphonium chloride were added into a round bottom flask and the temperature was decreased to 10° C. 0.78 g potassium tert-butoxide was added in batch, and the reaction was conducted for 30 min at 10° C. Then the temperature was maintained at 10° C., the solution of 3.7 g intermediate of formula 2-6 in tetrahydrofuran was added dropwise. Then the reaction was conducted at a temperature of 10 to 20° C. for 3 hours.

A proper amount of water was added and a phase separation was conducted, and the obtained organic phase was concentrated to dryness and then dissolved in hot petroleum ether. The obtained solution was filtered to remove the insoluble byproducts, and the filtrate was concentrated to remove the petroleum ether. The product was again dissolved in tetrahydrofuran, hydrochloric acid was added and the mixture was heated to reflux for 2 hours. After hydrolysis, the reaction mixture was cooled to room temperature, and water was added and the organic phase was separated in separating funnel. Then the organic phase was concentrated to dryness and subjected to a recrystallization in 50/50 mixture of toluene/ethyl acetate, to obtain the intermediate of formula 2-7; wherein the reaction is shown as follows:

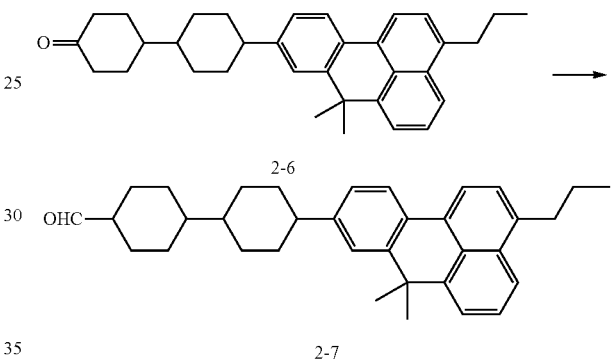

(g) 50 ml tetrahydrofuran and 1.85 g of methyl triphenyl phosphonium bromide was added to a round bottom flask, and the mixture was cooled to below 10° C., 0.70 g potassium tert-butoxide was added. The reaction was conducted at constant temperature of 10° C. for 30 min; then the temperature is maintained at 10° C. and the solution of 2.8 g of the compound of formula 2-7 obtained in Step (f) in tetrahydrofuran was added dropwise. The reaction was conducted for 3 hours at a temperature of 10 to 20° C., then water was added and the organic phase was separated in separating funnel. The organic phase obtained by phase separation was concentrated to dryness and again dissolved in hot petroleum ether. The obtained solution was filtered to remove the insoluble byproducts, and the filtrate was concentrated to remove the petroleum ether. The obtained product was subjected to a recrystallization in 50/50 mixture of toluene/ethyl acetate, to obtain a white crystal. The white crystal was determined by NMR and mass spectrometry (MS=476.36) to have the following structural formula 2-8; wherein the reaction is shown as follows:

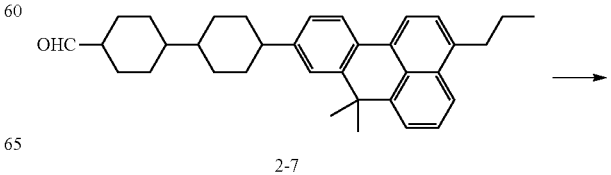

-continued

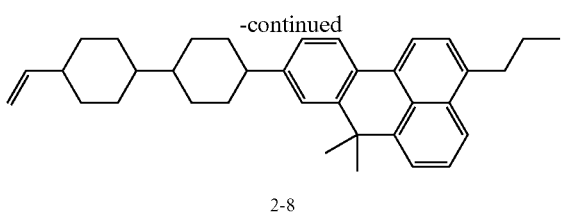

2-8

The NMR spectrum of the liquid crystal compound is shown in FIG. 1. For the sake of simplicity, the obtained compound is represented by a compound 2-8 in the following; according to the IUPAC nomenclature, the obtained liquid crystal compound is named as 7,7-dimethyl-3-propyl-9-(4'-vinyl-[1,1'-bi-(cyclohexan)]-4-yl)-7H-benzo[de]anthracene.

The clearing point of the liquid crystal compound or composition is measured according to the test method of the clearing point of the liquid crystal material described in the Test Method of the Performances of Liquid Crystal Material issued by the Ministry of Information Industry of the People's Republic of China (SJ 20746-1999). According to the measurement, liquid crystal compound 2-8 obtained in above synthesis Example 1 has a clearing point of about 298° C.

The following non limiting Examples 2-9 are used to illustrate the liquid crystal compositions of the invention.

Examples 2-9

Liquid Crystal Composition

Table 1 shows the weight percentages of each compound contained in the liquid crystal composition of Examples 2 to 3, wherein compounds A, B, C, D, E, F and compound 2-8 obtained in the above synthesis Example 1 are defined as above. Table 1 also shows the measured values of the clearing point of the liquid crystal compositions of Examples 2 to 3.

The liquid crystal compositions were obtained by mixing all the compounds according to the weight percentages shown in following Table 1.

TABLE 1

|       | A | B  | C  | D  | E  | F | 2-8 | Clearing point (°C) |
|-------|---|----|----|----|----|---|-----|---------------------|
| Ex. 2 | 3 | 9  | 11 | 30 | 20 | 5 | 22  | 140                 |
| Ex. 3 | 4 | 10 | 12 | 16 | 10 | 8 | 40  | 147                 |

It is clear from Table 1 that the liquid crystal compositions of Examples 2 and 3 containing liquid crystal compound 2-8 have a clearing point of 140° C. and 147° C., which are much higher than that of generally used liquid crystal compositions. Furthermore, both of the liquid crystal compositions of Examples 2 and 3 also have a good balance of the physical and chemical properties, such as stability, optical anisotropy, dielectric anisotropy, viscosity and electric resistance. The higher clearing point of the liquid crystal composition may greatly broaden the scope of applications of liquid crystal materials made using the liquid crystal composition.

Table 2 shows the weight percentage of each compound contained in the liquid crystal composition of Examples 4 to 9, wherein compounds A, B, C, D, E, F, G, P1 and compound 2-8 obtained in the above synthesis Example 1 are as above defined. Table 2 also shows the measurements of the clearing point of the liquid crystal compositions of Examples 4 to 9.

The liquid crystal compositions of Examples 4 to 9 were obtained by mixing all the compounds according to the weight percentages shown in following Table 2.

TABLE 2

|       | A  | B  | C  | D  | E  | F  | G  | P1 | 2-8 | Clearing point (°C) |
|-------|----|----|----|----|----|----|----|----|-----|---------------------|
| Ex. 4 | 5  | 12 | 12 | 12 | 10 | 8  | 9  | 23 | 9   | 146                 |
| Ex. 5 | 8  | 12 | 17 | 5  | 18 | 15 | 5  | 15 | 5   | 138                 |
| Ex. 6 | 10 | 15 | 18 | 5  | 20 | 6  | 6  | 15 | 5   | 137                 |
| Ex. 7 | 5  | 10 | 10 | 5  | 5  | 5  | 11 | 30 | 19  | 152                 |
| Ex. 8 | 4  | 8  | 10 | 13 | 5  | 8  | 30 | 15 | 7   | 140                 |
| Ex. 9 | 5  | 11 | 9  | 30 | 8  | 12 | 5  | 12 | 8   | 142                 |

From the data in Table 2, it is clear that the liquid crystal compositions containing the liquid crystal compound 2-8 have a clearing point above 137° C. This is generally higher than that of the conventional liquid crystal compositions. Furthermore, all the liquid crystal compositions of Examples 4 to 9 also have a good balance of the physical and chemical properties, such as stability, optical anisotropy, dielectric anisotropy, viscosity and electric resistance. The higher clearing point of the liquid crystal composition greatly improves the scope of applications of the produced liquid crystal materials made of the liquid crystal composition.

Comparative Examples 10 and 11

The compositions of Comparative Examples 10 and 11 were prepared according to the weight content of each compound in Examples 3 and 4, but the difference was that, in Comparative Examples 10 and 11, compound P1 was used to replace compound 2-8 in Examples 3 and 4:

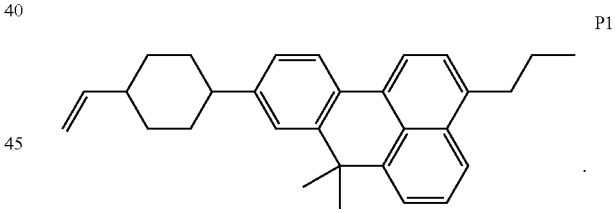

P1

The clearing point of compound P1 was measured to be about 250° C., which is lower than that of compound 2-8. Furthermore, the clearing point of the compositions of Comparative Examples 10 and 11 were measured to have clearing points of 125° C. and 127° C. respectively, which are also lower than that of the composition of Examples 3 and 4.

Although the present disclosure has been described with reference to specific embodiments, it should be understood that the limitations of the described embodiments are provided merely for purpose of illustration and are not intended to limit the present invention and associated general inventive concepts. Instead, the scope of the present invention is defined by the appended claims, and all variations and equivalents that fall within the range of the claims are intended to be embraced therein. Thus, other embodiments than the specific exemplary ones described herein are equally possible within the scope of these appended claims.

The invention claimed is:

1. A liquid crystal compound, having general formula P2:

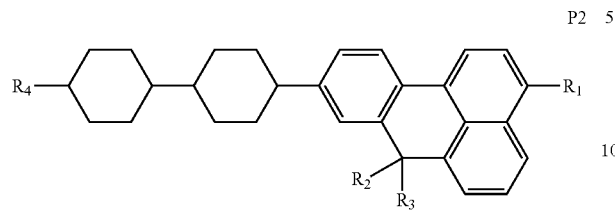

wherein, R1 is C1-C6 alkyl, R2 and R3, independently are C1-C6 alkyl, and R4 is C2-C6 alkenyl.

2. The liquid crystal compound according to claim 1, wherein R1 is C2-C4 alkyl, R2 and R3, independently are C1-C3 alkyl, and R4 is C2-C3 alkenyl.

3. The liquid crystal compound according to claim 1, wherein the liquid crystal compound has the following structural formula:

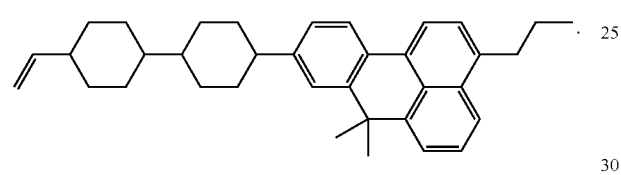

4. A liquid crystal composition, comprising 5% to 40% by weight of a liquid crystal compound according to claim 1, relative to the total weight of the liquid crystal composition.

5. The liquid crystal composition according to claim 4, comprising: 20% to 40% by weight of a liquid crystal compound according to claim 1:

2% to 8% by weight of compound A:

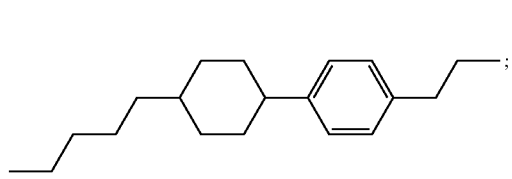

8% to 19% by weight of compound B:

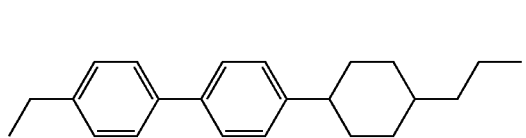

10% to 20% by weight of compound C:

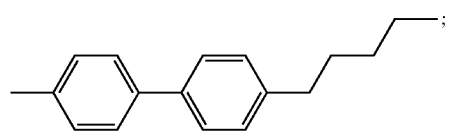

15% to 30% by weight of compound D:

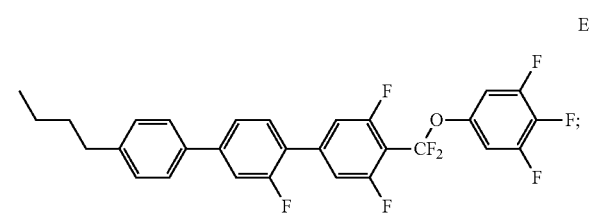 [SMILES: CCCCc1ccc(-c2ccc(-c3cc(F)c(C(F)(F)Oc4cc(F)c(F)c(F)c4)c(F)c3)c(F)c2)cc1]

8% to 20% by weight of compound E:

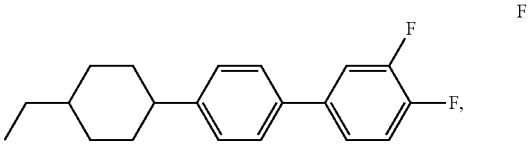 [SMILES: CCC1CCC(c2ccc(-c3ccc(F)c(F)c3)cc2)CC1]

5% to 15% by weight of compound F:

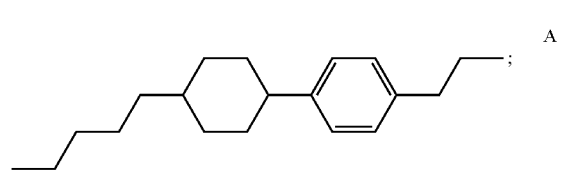 [SMILES: CCCCCC1CCC(c2ccc(CCC)cc2)CC1]

relative to the total weight of the liquid crystal composition.

6. The liquid crystal composition according to claim 4, wherein the liquid crystal composition comprises 6% by weight of compound A, 15% by weight of compound B, 15% by weight of compound C, 20% by weight of compound D, 10% by weight of compound E, 9% by weight of compound F, and 25% by weight of a liquid crystal compound according to claim 1, relative to the total weight of the liquid crystal compound.

7. The liquid crystal composition according to claim 4, wherein the liquid crystal composition comprises, 5% to 20% by weight of a liquid crystal compound according to claims 1:

3% to 10% by weight of compound A

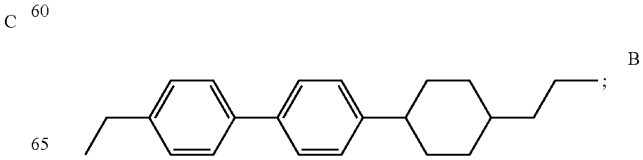

8% to 15% by weight of compound B:

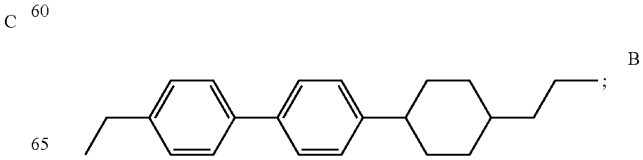

7% to 18% by weight of compound C:
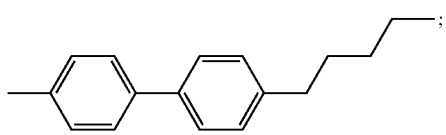
5% to 30% by weight of compound D
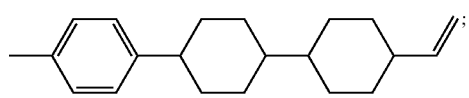
5% to 20% by weight of compound E:
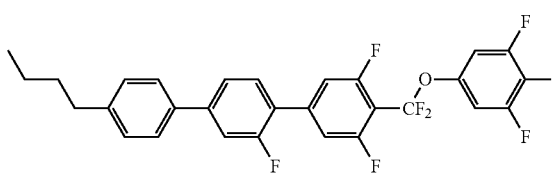
5% to 15% by weight of compound F:
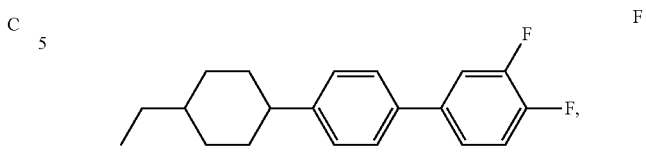
5% to 30% by weight of compound G:
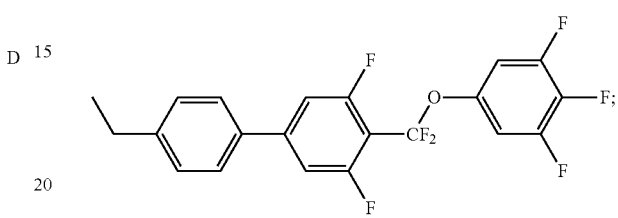
15% to 30% by weight of compound P1:
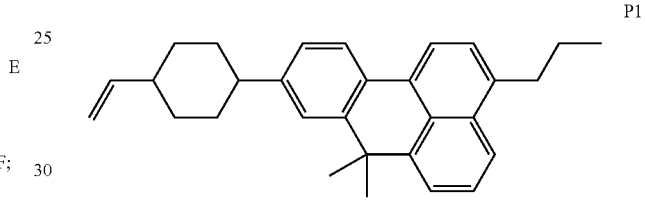
relative to the total weight of the liquid crystal composition.
* * * * *